US009388429B2

(12) United States Patent
Gall et al.

(10) Patent No.: US 9,388,429 B2
(45) Date of Patent: Jul. 12, 2016

(54) METHOD FOR PROPAGATING ADENOVIRAL VECTORS ENCODING INHIBITORY GENE PRODUCTS

(71) Applicant: GenVec, Inc., Gaithersburg, MD (US)

(72) Inventors: Jason G. D. Gall, Germantown, MD (US); Douglas E. Brough, Gaithersburg, MD (US); C. Richter King, New York, NY (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 14/288,493

(22) Filed: May 28, 2014

(65) Prior Publication Data

US 2014/0273228 A1     Sep. 18, 2014

Related U.S. Application Data

(63) Continuation of application No. 12/118,008, filed on May 9, 2008, which is a continuation of application No. PCT/US2006/060732, filed on Nov. 8, 2006.

(60) Provisional application No. 60/735,578, filed on Nov. 10, 2005.

(51) Int. Cl.
| | |
|---|---|
| C12N 7/01 | (2006.01) |
| C12N 15/861 | (2006.01) |
| C12N 15/86 | (2006.01) |
| C12N 7/00 | (2006.01) |
| C12N 15/63 | (2006.01) |

(52) U.S. Cl.
CPC *C12N 15/86* (2013.01); *C12N 7/00* (2013.01); *C12N 15/635* (2013.01); *C12N 2710/10343* (2013.01); *C12N 2710/10352* (2013.01); *C12N 2830/006* (2013.01)

(58) Field of Classification Search
None
See application file for complete search history.

(56) References Cited

U.S. PATENT DOCUMENTS

| 6,251,640 | B1 | 6/2001 | Yao |
| 6,391,612 | B1 | 5/2002 | Bruder et al. |
| 2005/0267061 | A1 | 12/2005 | Martin |

OTHER PUBLICATIONS

Gao, W. et al., "Effects of a SARS-associated coronavirus vaccine in monkeys", 2003, Lancet, vol. 362: pp. 1895-1896.*
Mayr, G. et al., "Immune responses and protection against foot-and-mouth disease virus (FMDV) challenge in swine vaccinated with adenovirus-FMDV constructs", 2001, Vaccine, vol. 19: pp. 2152-2162.*
Ablack et al., "Comparison of E1A CR3-Dependent Transcriptional Activation Across Six Different Human Adenovirus Subgroups," *J. Virol.*, 84 (24), 12771-12781 (Dec. 2010).
Brough et al., "A Gene Transfer Vector-Cell Line System for Complete Functional Complementation of Adenovirus Early Regions E1 and E4," *J. Virol.*, 70 (9), 6497-6501 (Sep. 1996).
Brunner et al., "Site-directed Mutagenesis of Cysteine Residues in the Pro Region of the Transforming Growth Factor β1 Precursor," *J. Biol. Chem.*, 264 (23), 13660-13664 (Aug. 15, 1989).
Carlson et al., "Molecular Characterization of a Putative Antiretroviral Transcriptional Factor, OTK18," *The Journal of Immun.*, 172, 381-391 (2004).
Edholm et al., "Adenovirus Vector Designed for Expression of Toxic Proteins," *J. Virol.*, 75 (20), 9579-9584 (Oct. 2001).
Farina et al., "Replication-defective vector-based on a chimpanzee adenovirus," *J. Virol.* 75: 11603-11613 (2001).
Gall et al., "Rescue and Production of Vaccine and Therapeutic Adenovirus Vectors Expressing Inhibitory Transgenes," *Molecular Biotechnology*, 35, 263-273 (2007).
GenBank Accession No. J01830, GI No. 154846, Jul. 8, 2002.
Gossen et al., "Tight Control of Gene Expression in Mammalian Cells by Tetracycline-Responsive Promoters," *Proc. Natl. Acad. Sci. USA*, 89, 5547-5551 (Jun. 1992).
Goukassian et al., "Overexpression of p27$^{Kip1}$ by Doxycycline-Regulated Adenoviral Vectors Inhibits Endothelial Cell Proliferation and Migration and Impairs Angiogenesis," *FASEB J.* ,15, 1877-1885 (2001).
Hartl et al., "Adenovirus type 5 early region 1B 55-kDa Oncoprotein Can Promote Cell Transformation by a Mechanism Independent from Blocking p53-activated Transcription," *Oncogene*, 27, 3673-3684 (2008).
Hillen et al., "Tet Repressor-Tet Operator Interaction," *Protein-Nucleic Acid Interaction, Topics in Molecular and Structural Biology*, Saenger et al., eds., vol. 10, 143-162, Macmillan, London (1989).
Hu et al., "Development of an Adenovirus Vector with Tetracycline-Regulatable Human Tumor Necrosis Factor α Gene Expression," *Cancer Res.*, 57, 3339-3343 (Aug. 15, 1997).
Jiang et al., "Adenovirus Expressing RIZ1 in Tumor Suppressor Gene Therapy of Microsatellite-unstable Colorectal Cancers," *Cancer Research*, 61, 1796-1798 (2001).
Kalos et al., "Position-independent transgene expression mediated by boundary elements from the apolipoprotein B chromatin domain," *Mol. Cell. Biol.*, 15: 198-207 (1995).
Kang et al., "Novel Cancer Antiangiotherapy Using the VEGF Promoter-targeted Artificial Zinc-Finger Protein and Oncolytic Adenovirus," *Mol. Ther.*, 16 (6), 1033-1040 (Jun. 2008).
Marinovic et al., "Ubiquitin (UbC) Expression in Muscle cells Is Increased by Glucocorticoids through a Mechanism Involving Sp1 and MEK1," *J. Biol. Chem.*, 277 (19), 16673-16681 (2002).
Massie et al., "Inducible Overexpression of a Toxic Protein by an Adenovirus Vector with a Tetracyclune-Regulatable Expression Casette," *J. Virol.*, 72 (3), 2289-2296 (Mar. 1998).

(Continued)

*Primary Examiner* — Michael Burkhart
(74) *Attorney, Agent, or Firm* — Leydig, Voit & Mayer, Ltd.

(57) ABSTRACT

The invention provides a method of propagating an adenoviral vector. The method comprises (a) providing a cell comprising a cellular genome comprising a nucleic acid sequence encoding a tetracycline operon repressor protein (tetR), and (b) contacting the cell with an adenoviral vector comprising a heterologous nucleic acid sequence encoding a toxic protein. The heterologous nucleic acid sequence is operably linked to a promoter and one or more tetracycline operon operator sequences (tetO), and expression of the heterologous nucleic acid sequence is inhibited in the presence of tetR, such that the adenoviral vector is propagated. The invention also provides a system comprising the aforementioned cell and adenoviral vector.

22 Claims, No Drawings

(56) References Cited

OTHER PUBLICATIONS

Matthews et al., "Development and Use of a 293 Cell Line Expressing lac repressor for the Rescue of Recombinant Adenoviruses Expressing High Levels of Rabies Virus Glycoprotein," *J. Gen. Virol.*, 80, 345-353 (1999).

Mizuguchi et al., "Characteristics of Adenovirus-Mediated Tetracycline-Controllable Expression System," *Biochim. Biophys. Acta*, 1568, 21-29 (2001).

Molin et al., "Overexpression of Essential Splicing Factor ASF/SF2 Blocks the Temporal Shift in Adenovirus Pre-mRNA Splicing and Reduces Virus Progeny Formation," *J. Virol.*, 74 (19), 9002-9009 (Oct. 2000).

Molin et al., "Two Novel Adenovirus Vector Systems Permitting Regulated Protein Expression in Gene Transfer Experiments," *J. Virol.*, 72 (10), 8358-8361 (Oct. 1998).

Nicolas et al., "Creation and Repair of Specific DNA Double-Strand Breaks in Vivo Following Infection with Adenovirus Vectors Expressing *Saccharomyces cerevisiae* HO Endonuclease," *Virology*, 266, 211-224 (2000).

Price et al., "Gene Transfer of an Engineered Transcription Factor Promoting Expression of VEGF-A Protects Against Experimental Diabetic Neuropathy," *Diabetes*, 55, 1847-1854 (2006).

Rasmussen et al., "TNFerade Biologic: Preclinical toxicology of a Novel Adenovector with a Radiation-Inducible Promoter, carrying the Human Tumor Necrosis Factor Alpha Gene," *Cancer Gene Ther.*, 9, 951-957 (2002).

Rubinchik et al., "A Complex Adenovirus Vector That Delivers FASL-GFP with Combined Prostate-Specific and Tetracycline-Regulated Expression," *Mol. Ther.*, 4(5), 416-426 (Nov. 2001).

Shears et al., "Efficient Inhibition of Intimal Hyperplasia by Adenovirus-Mediated Inducible Nitric Oxide Synthase Gene Transfer to Rats and Pigs In Vivo," *J. Am. Coll. Surg.*, 187, 295-306 (1998).

Shockett et al., "Diverse Strategies for Tetracycline-Regulated Inducible Gene Expression," *Proc. Natl. Acad. Sci. USA*, 93, 5173-5176 (May 1996).

T-REX-293 Product Page, Invitrogen Corporation, 2 pages (printed Jun. 21, 2010).

Wagner et al., "Nucleotide Sequence of the Thymidine Kinase Gene of Herpes Simples Virus Type 1," *Proc. Natl. Acad. Sci. USA*, 78 (3), 1441-1445 (Mar. 1981).

Wang et al., "Local Adenoviral-Mediated Inducible Nitric Oxide Synthase Gene Trasnfer Inhibits Neointimal Formation in the Porcine Coronary Stented Model," *Mol. Ther.*, 7, 597-603 (2003).

Wickham et al., "Increased In Vitro and In Vivo Gene Transfer by Adenovirus Vectors Containing Chimeric Fiber Proteins," *J. Virol.*, 71 (11), 8221-8229 (Nov. 1997).

Xu et al., "A Versatile Framework for the Design of Ligand-Dependent, Transgene-Specific Transcription Factors," *Mol. Ther.*, 3 (2), 262-273 (Feb. 2001).

Yang et al., "Selective Modification of Variable Loops Alters Tropism and Enhances Immunogenicity of Human Immunodeficiency Virus Type 1 Envelope," *J. Virol.*, 78 (8), 4029-4036 (Apr. 2004).

Yu et al, "Inducible Human Immunodeficiency Virus Type I packaging cell lines," *J. of Virology*, 70: 4530-4537 (1996).

U.S. Appl. No. 12/118,008, filed May 9, 2008.

* cited by examiner

METHOD FOR PROPAGATING ADENOVIRAL VECTORS ENCODING INHIBITORY GENE PRODUCTS

CROSS-REFERENCE TO RELATED APPLICATIONS

This patent application is a continuation of copending U.S. application Ser. No. 12/118,008, filed May 9, 2008, which is a continuation of International Patent Application No. PCT/US2006/060732, filed Nov. 8, 2006, designating the United States, which claims the benefit of U.S. Provisional Patent Application No. 60/735,578, filed Nov. 10, 2005.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,345 Byte ASCII (Text) file named "716586_ST25.txt" created on May 27, 2014.

BACKGROUND OF THE INVENTION

Delivery of proteins as therapeutics or for inducing an immune response in biologically relevant amounts has been an obstacle to drug and vaccine development for decades. One solution that has proven to be a successful alternative to traditional drug delivery approaches is delivery of exogenous nucleic acid sequences for production of therapeutic factors in vivo. Gene transfer vectors ideally enter a wide variety of cell types, have the capacity to accept large nucleic acid sequences, are safe, and can be produced in quantities required for treating patients. Viral vectors have these advantageous properties and are used in a variety of protocols to treat or prevent biological disorders.

Adenoviral vectors are attractive for gene transfer applications, such as gene therapy and vaccines as a result of their ability to infect a variety of cell types with high efficiency. Adenoviral vectors containing a heterologous transgene under the control of astrong promoter are potent, achieving expression of the heterologous protein up to 20% of total cell proteins (see, e.g., Massie et al., *J. Virol.*, 72, 2289-2296 (1998)). A high level of transgene expression, however, often is inhibitory to virus growth, such as when the transgene encodes a protein that is cytotoxic to a packaging cell. Thus, high expression of an adenovirus-encoded transgene can prevent the production of viable adenoviral vector particles from naked DNA (see, e.g., Matthews et al., *J. Gen. Virol.*, 80 (Pt 2), 345-353 (1999)), or reduce the productivity of virus growth within packaging cells (see, e.g., Molin et al., *J. Virol.*, 74, 9002-9009 (2000)).

To better regulate transgene expression within virus packaging cells while maintaining vector potency, gene regulation systems have been employed in the construction of adenoviral vectors. These systems typically incorporate transcriptional regulatory proteins into the adenoviral vector or in the target cell (see, e.g., Massie et al., supra, Goukassian et al., *FASEB J.*, 15, 1877-1885 (2001), Mizuguchi et al., *Biochim. Biophys. Acta*, 1568, 21-29 (2001), Rubinchik et al., *Mol. Ther.*, 4, 416-426 (2001), Molin et al., *J. Virol.*, 72, 8358-8361 (1998), Hu et al., *Cancer Res.*, 57, 3339-3343 (1997), Edholm et al., *J. Virol.*, 75, 9579-9584 (2001), and U.S. Pat. No. 6,391,612). Such gene regulation systems, however, often require the use of inducer compounds (e.g., tetracycline analogs), which increases the time required to generate viable adenoviral vector particles, thereby complicating their widespread use.

Therefore, there remains a need for more efficient methods of propagating adenoviral vectors encoding transgenes whose expression inhibits viral growth in host cells. The invention provides such a method. These and other advantages of the invention, as well as additional inventive features, will be apparent from the description of the invention provided herein.

BRIEF SUMMARY OF THE INVENTION

The invention provides a method of propagating an adenoviral vector, which method comprises (a) providing a cell comprising a cellular genome comprising a nucleic acid sequence encoding a tetracycline operon repressor protein (tetR), and (b) contacting the cell with an adenoviral vector having an adenoviral genome comprising a heterologous nucleic acid sequence encoding a protein that is toxic to the cell, wherein the heterologous nucleic acid sequence is operably linked to a promoter and one or more tetracycline operon operator sequences (tetO), so as to transfect the cell with the adenoviral vector. The nucleic acid sequence encoding tetR is expressed to produce tetR, expression of the heterologous nucleic acid sequence is inhibited in the presence of tetR, and the adenoviral vector is propagated.

The invention also provides a system comprising (a) a cell comprising a cellular genome comprising a nucleic acid sequence encoding a tetracycline operon repressor protein (tetR), which can be expressed to produce tetR, and (b) an adenoviral vector having an adenoviral genome comprising a heterologous nucleic acid sequence encoding a protein that is toxic to the cell. The heterologous nucleic acid sequence is operably linked to a promoter and one or more tetracycline operon operator sequences (tetO), and the adenoviral vector can transfect the cell and be propagated in the cell.

DETAILED DESCRIPTION OF THE INVENTION

The invention is predicated, at least in part, on the discovery that adenoviral vectors encoding inhibitory gene products can be produced using a tetracycline operon-based gene regulation system in which regulation of gene expression is mediated through the packaging cell line, wherein the addition of inducer compounds is not required.

The invention provides a method of propagating an adenoviral vector. Adenovirus from various origins, subtypes, or mixture of subtypes can be used as the source of the viral genome for the adenoviral vector. While non-human adenovirus (e.g., simian, avian, canine, ovine, or bovine adenoviruses) can be used to generate the adenoviral vector, a human adenovirus preferably is used as the source of the viral genome for the adenoviral vector of the inventive method. Adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 are available from the American Type Culture Collection (ATCC, Manassas, Va.). Preferably, in the context of the inventive method, the adenoviral vector is of human subgroup C, especially serotype 2 or even more desirably serotype 5. However, non-group C adenoviruses can be used to prepare adenoviral gene transfer vectors for delivery of gene products to host cells. Preferred adenoviruses used in the construction of non-group C adenoviral gene transfer vectors include Ad12 (group A), Ad7 and Ad35 (group B), Ad30 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849,561 and International Patent Applications WO 97/12986 and WO 98/53087.

The adenoviral vector can comprise a mixture of subtypes and thereby be a "chimeric" adenoviral vector. A chimeric adenoviral vector can comprise an adenoviral genome that is derived from two or more (e.g., 2, 3, 4, etc.) different adenovirus serotypes. In the context of the invention, a chimeric adenoviral vector can comprise approximately equal amounts of the genome of each of the two or more different adenovirus serotypes. When the chimeric adenoviral vector genome is comprised of the genomes of two different adenovirus serotypes, the chimeric adenoviral vector genome preferably comprises no more than about 70% (e.g., no more than about 65%, about 50%, or about 40%) of the genome of one of the adenovirus serotypes, with the remainder of the chimeric adenovirus genome being derived from the genome of the other adenovirus serotype. In one embodiment, the chimeric adenoviral vector can contain an adenoviral genome comprising a portion of a serotype 2 genome and a portion of a serotype 5 genome. For example, nucleotides 1-456 of such an adenoviral vector can be derived from a serotype 2 genome, while the remainder of the adenoviral genome can be derived from a serotype 5 genome.

The adenoviral vector of the invention can be replication-competent. For example, the adenoviral vector can have a mutation (e.g., a deletion, an insertion, or a substitution) in the adenoviral genome that does not inhibit viral replication in host cells. The inventive adenoviral vector also can be conditionally replication-competent. Preferably, however, the adenoviral vector is replication-deficient in host cells.

By "replication-deficient" is meant that the adenoviral vector requires complementation of one or more regions of the adenoviral genome that are required for replication, as a result of, for example a deficiency in at least one replication-essential gene function (i.e., such that the adenoviral vector does not replicate in typical host cells, especially those in a human patient that could be infected by the adenoviral vector in the course of the inventive method). A deficiency in a gene, gene function, gene, or genomic region, as used herein, is defined as a deletion of sufficient genetic material of the viral genome to obliterate or impair the function of the gene (e.g., such that the function of the gene product is reduced by at least about 2-fold, 5-fold, 10-fold, 20-fold, 30-fold, or 50-fold) whose nucleic acid sequence was deleted in whole or in part. Deletion of an entire gene region often is not required for disruption of a replication-essential gene function. However, for the purpose of providing sufficient space in the adenoviral genome for one or more transgenes, removal of a majority of a gene region may be desirable. While deletion of genetic material is preferred, mutation of genetic material by addition or substitution also is appropriate for disrupting gene function. Replication-essential gene functions are those gene functions that are required for replication (e.g., propagation) and are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA1 and/or VA-RNA-2).

The replication-deficient adenoviral vector desirably requires complementation of at least one replication-essential gene function of one or more regions of the adenoviral genome. Preferably, the adenoviral vector requires complementation of at least one gene function of the E1A region, the E1B region, or the E4 region of the adenoviral genome required for viral replication (denoted an E1-deficient or E4-deficient adenoviral vector). In addition to a deficiency in the E1 region, the recombinant adenovirus also can have a mutation in the major late promoter (MLP), as discussed in International Patent Application Publication WO 00/00628. Most preferably, the adenoviral vector is deficient in at least one replication-essential gene function (desirably all replication-essential gene functions) of the E1 region and at least one gene function of the nonessential E3 region (e.g., an Xba I deletion of the E3 region) (denoted an E1/E3-deficient adenoviral vector). With respect to the E1 region, the adenoviral vector can be deficient in part or all of the E1A region and/or part or all of the E1B region, e.g., in at least one replication-essential gene function of each of the E1A and E1B regions, thus requiring complementation of the E1A region and the E1B region of the adenoviral genome for replication. The adenoviral vector also can require complementation of the E4 region of the adenoviral genome for replication, such as through a deficiency in one or more replication-essential gene functions of the E4 region.

When the adenoviral vector is E1-deficient, the adenoviral vector genome can comprise a deletion beginning at any nucleotide between nucleotides 335 to 375 (e.g., nucleotide 356) and ending at any nucleotide between nucleotides 3,310 to 3,350 (e.g., nucleotide 3,329) or even ending at any nucleotide between 3,490 and 3,530 (e.g., nucleotide 3,510) (based on the adenovirus serotype 5 genome).

When E2A-deficient, the adenoviral vector genome can comprise a deletion beginning at any nucleotide between nucleotides 22,425 to 22,465 (e.g., nucleotide 22,443) and ending at any nucleotide between nucleotides 24,010 to 24,050 (e.g., nucleotide 24,032) (based on the adenovirus serotype 5 genome). When E3-deficient, the adenoviral vector genome can comprise a deletion beginning at any nucleotide between nucleotides 28,575 to 29,615 (e.g., nucleotide 28,593) and ending at any nucleotide between nucleotides 30,450 to 30,490 (e.g., nucleotide 30,470) (based on the adenovirus serotype 5 genome).

When the adenoviral vector is deficient in at least one replication-essential gene function in one region of the adenoviral genome (e.g., an E1- or E1/E3-deficient adenoviral vector), the adenoviral vector is referred to as "singly replication-deficient." A particularly preferred singly replication-deficient adenoviral vector is, for example, a replication-deficient adenoviral vector requiring, at most, complementation of the E1 region of the adenoviral genome, so as to propagate the adenoviral vector (e.g., to form adenoviral vector particles).

The adenoviral vector of the invention can be "multiply replication-deficient," meaning that the adenoviral vector is deficient in one or more replication-essential gene functions in each of two or more regions of the adenoviral genome, and requires complementation of those functions for replication. For example, the aforementioned E1-deficient or E1/E3-deficient adenoviral vector can be further deficient in at least one replication-essential gene function of the E4 region (denoted an E1/E4- or E1/E3/E4-deficient adenoviral vector), and/or the E2 region (denoted an E1/E2- or E1/E2/E3-deficient adenoviral vector), preferably the E2A region (denoted an E1/E2A- or E1/E2A/E3-deficient adenoviral vector). An adenoviral vector deleted of the entire E4 region can elicit a lower host immune response. When E4-deficient, the adenoviral vector genome can comprise a deletion beginning at, for example, any nucleotide between nucleotides 32,805 to 32,845 (e.g., nucleotide 32,826) and ending at, for example, any nucleotide between nucleotides 35,540 to 35,580 (e.g., nucleotide 35,561) (based on the adenovirus serotype 5 genome), optionally in addition to deletions in the E1 region (e.g., nucleotides 356 to 3,329 or nucleotides 356 to 3,510) (based on the adenovirus serotype 5 genome) and/or deletions in the E3 region (e.g., nucleotides 28,594 to 30,469 or nucleotides 28,593 to 30,470) (based on the adenovirus serotype 5 genome). The endpoints defining the deleted nucleotide portions can be difficult to precisely determine and typically will not significantly affect the nature of the adenoviral vector, i.e., each of the aforementioned nucleotide numbers can be +/−1, 2, 3, 4, 5, or even 10 or 20 nucleotides.

If the adenoviral vector of the invention is deficient in a replication-essential gene function of the E2A region, the vector preferably does not comprise a complete deletion of the E2A region, which deletion preferably is less than about 230 base pairs in length. Generally, the E2A region of the adenovirus codes for a DBP (DNA binding protein), a polypeptide required for DNA replication. DBP is composed of 473 to 529 amino acids depending on the viral serotype. It is believed that DBP is an asymmetric protein that exists as a prolate ellipsoid consisting of a globular Ct with an extended Nt domain. Studies indicate that the Ct domain is responsible for DBP's ability to bind to nucleic acids, bind to zinc, and function in DNA synthesis at the level of DNA chain elongation. However, the Nt domain is believed to function in late gene expression at both transcriptional and post-transcriptional levels, is responsible for efficient nuclear localization of the protein, and also may be involved in enhancement of its own expression. Deletions in the Nt domain between amino acids 2 to 38 have indicated that this region is important for DBP function (Brough et al., *Virology*, 196, 269-281 (1993)). While deletions in the E2A region coding for the Ct region of the DBP have no effect on viral replication, deletions in the E2A region which code for amino acids 2 to 38 of the Nt domain of the DBP impair viral replication. It is preferable that any multiply replication-deficient adenoviral vector contains this portion of the E2A region of the adenoviral genome. In particular, for example, the desired portion of the E2A region to be retained is that portion of the E2A region of the adenoviral genome which is defined by the 5' end of the E2A region, specifically positions Ad5(23816) to Ad5(24032) of the E2A region of the adenoviral genome of serotype Ad5. This portion of the adenoviral genome desirably is included in the adenoviral vector because it is not complemented in current E2A cell lines so as to provide the desired level of viral propagation.

While the above-described deletions are described with respect to an adenovirus serotype 5 genome, one of ordinary skill in the art can determine the nucleotide coordinates of the same regions of other adenovirus serotypes, such as an adenovirus serotype 2 genome, without undue experimentation, based on the similarity between the genomes of various adenovirus serotypes, particularly adenovirus serotypes 2 and 5.

In one embodiment of the inventive method, the adenoviral vector can comprise an adenoviral genome deficient in one or more replication-essential gene functions of each of the E1 and E4 regions (i.e., the adenoviral vector is an E1/E4-deficient adenoviral vector), preferably with the entire coding region of the E4 region having been deleted from the adenoviral genome. In other words, all the open reading frames (ORFs) of the E4 region have been removed. Most preferably, the adenoviral vector is rendered replication-deficient by deletion of all of the E1 region and by deletion of a portion of the E4 region. The E4 region of the adenoviral vector can retain the native E4 promoter, polyadenylation sequence, and/or the right-side inverted terminal repeat (ITR).

It should be appreciated that the deletion of different regions of the adenoviral vector can alter the immune response of the mammal. In particular, deletion of different regions can reduce the inflammatory response generated by the adenoviral vector. Furthermore, the adenoviral vector's coat protein can be modified so as to decrease the adenoviral vector's ability or inability to be recognized by a neutralizing antibody directed against the wild-type coat protein, as described in International Patent Application WO 98/40509. Such modifications are useful for long-term treatment of persistent ocular disorders.

The adenoviral vector, when multiply replication-deficient, especially in replication-essential gene functions of the E1 and E4 regions, can include a spacer sequence to provide viral growth in a complementing cell line similar to that achieved by singly replication-deficient adenoviral vectors, particularly an E1-deficient adenoviral vector. In a preferred E4-deficient adenoviral vector of the invention wherein the L5 fiber region is retained, the spacer is desirably located between the L5 fiber region and the right-side ITR. More preferably in such an adenoviral vector, the E4 polyadenylation sequence alone or, most preferably, in combination with another sequence exists between the L5 fiber region and the right-side ITR, so as to sufficiently separate the retained L5 fiber region from the right-side ITR, such that viral production of such a vector approaches that of a singly replication-deficient adenoviral vector, particularly a singly replication-deficient E1 deficient adenoviral vector.

The spacer sequence can contain any nucleotide sequence or sequences which are of a desired length, such as sequences at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs in length. The spacer sequence can be coding or non-coding and native or non-native with respect to the adenoviral genome, but does not restore the replication-essential function to the deficient region. The spacer can also contain a promoter-variable expression cassette. More preferably, the spacer comprises an additional polyadenylation sequence and/or a passenger gene. Preferably, in the case of a spacer inserted into a region deficient for E4, both the E4 polyadenylation sequence and the E4 promoter of the adenoviral genome or any other (cellular or viral) promoter remain in the vector. The spacer is located between the E4 polyadenylation site and the E4 promoter, or, if the E4 promoter is not present in the vector, the spacer is proximal to the right-side ITR. The spacer can comprise any suitable polyadenylation sequence. Examples of suitable polyadenylation sequences include synthetic optimized sequences, BGH (Bovine Growth Hormone), polyoma virus, TK (Thymidine Kinase), EBV (Epstein Barr Virus) and the papillomaviruses, including human papillomaviruses and BPV (Bovine Papilloma Virus). Preferably, particularly in the E4 deficient region, the spacer includes an SV40 polyadenylation sequence. The SV40 polyadenylation sequence allows for higher virus production levels of multiply replication deficient adenoviral vectors. In the absence of a spacer, production of fiber protein and/or viral growth of the multiply replication-deficient adenoviral vector is reduced by comparison to that of a singly replication-deficient adenoviral vector. However, inclusion of the spacer in at least one of the deficient adenoviral regions, preferably the E4 region, can counteract this decrease in fiber protein production and viral growth. Ideally, the spacer is composed of the glucuronidase gene. The use of a spacer in an adenoviral vector is further described in, for example, U.S. Pat. No. 5,851,806 and International Patent Application WO 97/21826.

It has been observed that an at least E4-deficient adenoviral vector expresses a transgene at high levels for a limited amount of time in vivo and that persistence of expression of a transgene in an at least E4-deficient adenoviral vector can be modulated through the action of a trans-acting factor, such as HSV ICP0, Ad pTP, CMV-IE2, CMV-IE86, HIV tat, HTLV-tax, HBV-X, AAV Rep 78, the cellular factor from the U205 osteosarcoma cell line that functions like HSV ICP0, or the cellular factor in PC12 cells that is induced by nerve growth factor, among others, as described in for example, U.S. Pat. Nos. 6,225,113, 6,649,373, and 6,660,521, and International Patent Application Publication WO 00/34496. In view of the above, a multiply deficient adenoviral vector (e.g., the at least E4-deficient adenoviral vector) or a second expression vector can comprise a nucleic acid sequence encoding a trans-acting factor that modulates the persistence of expression of the nucleic acid sequence. Persistent expression of antigenic DNA can be desired when generating immune tolerance.

Desirably, the adenoviral vector requires, at most, complementation of replication-essential gene functions of the E1, E2A, and/or E4 regions of the adenoviral genome for replication (i.e., propagation). However, the adenoviral genome can be modified to disrupt one or more replication-essential gene functions as desired by the practitioner, so long as the adenoviral vector remains deficient and can be propagated using, for example, complementing cells and/or exogenous DNA (e.g., helper adenovirus) encoding the disrupted replication-essential gene functions. In this respect, the adenoviral vector can be deficient in replication-essential gene functions of only the early regions of the adenoviral genome, only the late regions of the adenoviral genome, and both the early and late regions of the adenoviral genome. Suitable replication-deficient adenoviral vectors, including singly and multiply replication-deficient adenoviral vectors, are disclosed in U.S. Pat. Nos. 5,837,511, 5,851,806, 5,994,106, 6,127,175, and 6,482,616; U.S. Patent Application Publications 2001/0043922 A1, 2002/0004040 A1, 2002/0031831 A1, 2002/0110545 A1, and 2004/0161848 A1; and International Patent Application Publications WO 94/28152, WO 95/02697, WO 95/16772, WO 95/34671, WO 96/22378, WO 97/12986, WO 97/21826, and WO 03/022311.

By removing all or part of, for example, the E1, E3, and E4 regions of the adenoviral genome, the resulting adenoviral vector is able to accept inserts of exogenous nucleic acid sequences while retaining the ability to be packaged into adenoviral capsids. The nucleic acid sequence can be positioned in the E1 region, the E3 region, or the E4 region of the adenoviral genome. Indeed, the nucleic acid sequence can be inserted anywhere in the adenoviral genome so long as the position does not prevent expression of the nucleic acid sequence or interfere with packaging of the adenoviral vector.

If the adenoviral vector is not replication-deficient, ideally the adenoviral vector is manipulated to limit replication of the vector to within a target tissue. The adenoviral vector can be a conditionally-replicating adenoviral vector, which is engineered to replicate under conditions pre-determined by the practitioner. For example, replication-essential gene functions, e.g., gene functions encoded by the adenoviral early regions, can be operably linked to an inducible, repressible, or tissue-specific transcription control sequence, e.g., promoter. In this embodiment, replication requires the presence or absence of specific factors that interact with the transcription control sequence. In autoimmune disease treatment, it can be advantageous to control adenoviral vector replication in, for instance, lymph nodes, to obtain continual antigen production and control immune cell production. Conditionally-replicating adenoviral vectors are described further in U.S. Pat. No. 5,998,205.

In addition to modification (e.g., deletion, mutation, or replacement) of adenoviral sequences encoding replication-essential gene functions, the adenoviral genome can contain benign or non-lethal modifications, i.e., modifications which do not render the adenovirus replication-deficient, or, desirably, do not adversely affect viral functioning and/or production of viral proteins, even if such modifications are in regions of the adenoviral genome that otherwise contain replication-essential gene functions. Such modifications commonly result from DNA manipulation or serve to facilitate expression vector construction. For example, it can be advantageous to remove or introduce restriction enzyme sites in the adenoviral genome. Such benign mutations often have no detectable adverse effect on viral functioning. For example, the adenoviral vector can comprise a deletion of nucleotides 10,594 and 10,595 (based on the adenoviral serotype 5 genome), which are associated with VA-RNA-1 transcription, but the deletion of which does not prohibit production of VA-RNA-1.

Similarly, the coat protein of a viral vector, preferably an adenoviral vector, can be manipulated to alter the binding specificity or recognition of a virus for a viral receptor on a potential host cell. For adenovirus, such manipulations can include deletion of regions of the fiber, penton, or hexon, insertions of various native or non-native ligands into portions of the coat protein, and the like. Manipulation of the coat protein can broaden the range of cells infected by a viral vector or enable targeting of a viral vector to a specific cell type.

For example, in one embodiment, the adenoviral vector comprises a chimeric coat protein (e.g., a fiber, hexon pIX, pIIIa, or penton protein), which differs from the wild-type (i.e., native) coat protein by the introduction of a nonnative amino acid sequence, preferably at or near the carboxyl terminus. Preferably, the nonnative amino acid sequence is inserted into or in place of an internal coat protein sequence. One of ordinary skill in the art will understand that the nonnative amino acid sequence can be inserted within the internal coat protein sequence or at the end of the internal coat protein sequence. The resultant chimeric viral coat protein is able to direct entry into cells of the adenoviral, vector comprising the coat protein that is more efficient than entry into cells of a vector that is identical except for comprising a wild-type adenoviral coat protein rather than the chimeric adenoviral coat protein. Preferably, the chimeric adenovirus coat protein binds a novel endogenous binding site present on the cell surface that is not recognized, or is poorly recognized, by a vector comprising a wild-type coat protein. One direct result of this increased efficiency of entry is that the adenovirus can bind to and enter numerous cell types which an adenovirus comprising wild-type coat protein typically cannot enter or can enter with only a low efficiency.

In another embodiment of the invention, the adenoviral vector comprises a chimeric virus coat protein not selective for a specific type of eukaryotic cell. The chimeric coat protein differs from the wild-type coat protein by an insertion of a nonnative amino acid sequence into or in place of an internal coat protein sequence. In this embodiment, the chimeric adenovirus coat protein efficiently binds to a broader range of eukaryotic cells than a wild-type adenovirus coat, such as described in International Patent Application WO 97/20051.

Specificity of binding of an adenovirus to a given cell can also be adjusted by use of an adenovirus comprising a short-shafted adenoviral fiber gene, as discussed in U.S. Pat. No. 5,962,311. Use of an adenovirus comprising a short-shafted adenoviral fiber gene reduces the level or efficiency of adenoviral fiber binding to its cell-surface receptor and increases adenoviral penton base binding to its cell-surface receptor, thereby increasing the specificity of binding of the adenovirus to a given cell. Alternatively, use of an adenovirus comprising a short-shafted fiber enables targeting of the adenovirus to a desired cell-surface receptor by the introduction of a nonnative amino acid sequence either into the penton base or the fiber knob.

Of course, the ability of an adenoviral vector to recognize a potential host cell can be modulated without genetic manipulation of the coat protein. For instance, complexing an adenovirus with a bispecific molecule comprising a penton base-binding domain and a domain that selectively binds a particular cell surface binding site enables one of ordinary skill in the art to target the vector to a particular cell type.

Suitable modifications to an adenoviral vector are described in U.S. Pat. Nos. 5,543,328, 5,559,099, 5,712,136, 5,731,190, 5,756,086, 5,770,442, 5,846,782, 5,871,727, 5,885,808, 5,922,315, 5,962,311, 5,965,541, 6,057,155, 6,127,525, 6,153,435, 6,329,190, 6,455,314, 6,465,253, 6,576,456, 6,649,407, 6,740,525; 6,951,755; U.S. Patent Application Publications 2001/0047081 A1, 2002/0013286 A1, 2002/0151027 A1, 2003/0022355 A1, 2003/0099619 A1, 2003/0166286 A1, and 2004/0161848 A1; and International Patent Applications WO 95/02697, WO 95/16772, WO 95/34671, WO 96/07734, WO 96/22378, WO 96/26281, WO 97/20051, WO 98/07865, WO 98/07877, WO 98/40509, WO 98/54346, WO 00/15823, WO 01/58940, and WO 01/92549. Similarly, it will be appreciated that numerous adenoviral vectors are available commercially. Construction of adenoviral vectors is well understood in the art. Adenoviral vectors can be constructed and/or purified using methods known in the art (e.g., using complementing cell lines, such as the 293 cell line, Per.C6 cell line, or 293-ORF6 cell line) and methods set forth, for example, in U.S. Pat. Nos. 5,965,358, 5,994,128, 6,033,908, 6,168,941, 6,329,200, 6,383,795, 6,440,728, 6,447,995, 6,475,757, 6,908,762, and 6,913,927; U.S. Patent Application Publications 2002/0034735 A1 and 2004/0063203 A1; and International Patent Applications WO 98/53087, WO 98/56937, WO 99/15686, WO 99/54441, WO 00/12765, WO 01/77304, and WO 02/29388, as well as the other references identified herein.

The adenoviral vector of the inventive method comprises an adenoviral genome comprising a heterologous nucleic acid sequence. A "heterologous nucleic acid sequence" is any nucleic acid sequence that is not obtained from, derived from, or based upon a naturally occurring nucleic acid sequence of the adenoviral vector. By "naturally occurring" is meant that the nucleic acid sequence can be found in nature and has not been synthetically modified. The heterologous nucleic acid sequence also is not obtained from, derived from, or based upon an adenoviral nucleic acid sequence. For example, the heterologous nucleic acid sequence can be a viral, bacterial, plant, or animal nucleic acid sequence. A sequence is "obtained" from a source when it is isolated from that source. A sequence is "derived" from a source when it is isolated from a source but modified in any suitable manner (e.g., by deletion, substitution (mutation), insertion, or other modification to the sequence) so as not to disrupt the normal function of the source gene. A sequence is "based upon" a source when the sequence is a sequence more than about 70% homologous (preferably more than about 80% homologous, more preferably more than about 90% homologous, and most preferably more than about 95% homologous) to the source but obtained through synthetic procedures (e.g., polynucleotide synthesis, directed evolution, etc.). Determining the degree of homology, including the possibility for gaps, can be accomplished using any suitable method (e.g., BLASTnr, provided by GenBank). Notwithstanding the foregoing, the nucleic acid sequence that makes up the heterologous nucleic acid sequence can be naturally found in the adenoviral vector, but located at a nonnative position within the adenoviral genome and/or operably linked to a nonnative promoter.

The adenoviral vector comprises at least one heterologous nucleic acid sequence as described herein, i.e., the adenoviral vector can comprise one heterologous nucleic acid sequence as described herein or more than one heterologous nucleic acid sequence as described herein (i.e., two or more of the heterologous nucleic acid sequences). The heterologous nucleic acid sequence preferably encodes a protein (i.e., one or more nucleic acid sequences encoding one or more proteins). An ordinarily skilled artisan will appreciate that any type of nucleic acid sequence (e.g., DNA, RNA, and cDNA) that can be inserted into an adenoviral vector can be used in connection with the invention.

In the context of the invention, the heterologous nucleic acid sequence can encode any suitable protein, but preferably encodes a protein that is toxic to the cell. Desirably, the protein is a bacterial protein, a viral protein, a plant protein, a parasite protein, a fungi protein, an animal protein, or an antibiotic. When the heterologous nucleic acid sequence encodes a bacterial protein, the protein can be isolated or derived from any suitable bacterium, including, but not limited to *Actinomyces, Anabaena, Bacillus, Bacteroides, Bdellovibrio, Caulobacter, Chlamydia, Chlorobium, Chromatium, Clostridium, Cytophaga, Deinococcus, Escherichia, Halobacterium, Heliobacter, Hyphomicrobium, Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema.* Desirably, the heterologous nucleic acid sequence encodes a toxin protein isolated or derived from *Bacillus anthracis* (e.g., protective antigen, lethal factor, or edema factor), *Bordetella pertussis* (e.g., adenylate cyclase toxin or pertussis toxin), *Vibrio cholerae* (e.g., cholera enterotoxin), *Escherichia coli* (e.g., ST toxin or LT toxin), *Shigella dysenteriae* (e.g., shiga toxin), *Clostridium perfringens* (e.g., perfringens enterotoxin), *Clostridium botulinum* (e.g., botulinum toxin), *Clostridium tetani* (e.g., tetanus toxin), *Corynebacterium diphtheriae* (e.g., diphtheria toxin), *Pseudomonas aeruginosa* (e.g., exotoxin A), *Staphylococcus aureus* (e.g., staphylococcus enterotoxins, toxic shock syndrome toxin, or exfoliatin toxin), or *Streptococcus pyogenes* (e.g., erythrogenic toxin).

The heterologous nucleic acid also can be encode a parasite protein, such as, but not limited to, a parasite of the phylum Sporozoa (also referred to as phylum Apicomplexa), Ciliophora, Rhizopoda, or Zoomastigophora. Preferably, the parasite is of the phylum Sporozoa and genus *Plasmodium.* The protein can be from any suitable *Plasmodium* species, but preferably is from a *Plasmodium* species that infects humans and causes malaria (e.g., *Plasmodium falciparum, Plasmodium vivax, Plasmodium ovale, Plasmodium malariae*). Suitable *Plasmodium* proteins include, for example, circumsporozoite protein (CSP), sporozoite surface protein 2

(SSP2), liver-stage antigen 1 (LSA-1), Pf exported protein 1 (PfExp-1)/Py hepatocyte erythrocyte protein 17 (PyHEP17), Pf Antigen 2, merozoite surface protein 1 (MSP-1), merozoite surface protein 2 (MSP-2), erythrocyte binding antigen 175 (EBA-175), ring-infected erythrocyte surface antigen (RESA), serine repeat antigen (SERA), glycophorin binding protein (GBP-130), histidine rich protein 2 (HRP-2), rhoptry-associated proteins 1 and 2 (RAP-1 and RAP-2), erythrocyte membrane protein 1 (PfEMP1), and apical membrane antigen 1 (AMA-1).

When the heterologous nucleic acid sequence encodes a virus protein, the protein can be isolated or derived from any suitable virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae (e.g., Hepatitis B virus), Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia virus), Reoviridae (e.g., rotavirus), Retroviridae (e.g., lentivirus, such as human immunodeficiency virus (HIV) 1 and HIV 2), Rhabdoviridae, Totiviridae, Crimean-Congo haemorrhagic fever virus, Eastern Equine Encephalitis virus, Hendra virus, Lassa fever virus, Monkeypox virus, Nipah virus, Rift Valley fever virus, South American Haemorrhagic Fever viruses, and Venezuelan Equine Encephalitis virus.

Preferably, at least one protein of the inventive method is a retroviral protein. The retroviral protein can be, for example, an HIV antigen, such as all or part of the gag, env, or pol proteins, or a fusion protein comprising any of the gag, env, or pol proteins. Any clade of HIV is appropriate for protein selection, including clades A, B, C, MN, and the like. Also preferably, at least one protein encoded by the heterologous nucleic acid sequence is a coronavirus protein, such as a SARS virus protein. Suitable SARS virus proteins for the inventive method include, for example, all or part of the E protein, the M protein, and the spike protein of the SARS virus. In another embodiment, at least one protein encoded by the heterologous nucleic acid sequence is an aphthovirus protein, such as a foot-and-mouth disease virus (FMDV) protein. Suitable FMDV proteins include, for example, proteins 1A, 1B, 1C, and 1D, collectively referred to as P1, which form the capsid proteins of the virus, proteins 2A, 2B, and 2C (collectively referred to as the P2 protein), and proteins 3A, 3B, 3C, and 3D (collectively referred to as the P3 protein). The FMDV protein also can be an empty virus capsid of FMDV. An "empty virus capsid" contains only the portion of the FMDV genome encoding the viral structural proteins and the 3C protein, which is required for capsid formation (see Mayr et al., *Virology*, 263: 496-506 (1999)), and does not contain infectious viral nucleic acid. Suitable viral proteins also include all or part of Dengue protein M, Dengue protein E, Dengue D1NS1, Dengue D1NS2, and Dengue D1NS3.

The viral peptides specifically recited herein are merely exemplary as any viral protein can be used in the context of the invention.

When the heterologous nucleic acid sequence encodes a fungal protein, the protein can be isolated or obtained from any of the following genuses: *Coccidioides, Candida, Cryptococcus, Trichosporon, Acremonium, Cladophialophora, Pseudallescheria, Rizopus, Scedosporium, Aspergillus, Aureobasidium, Bipolaris, Fusarium, Phialophora, Blastomyces, Histoplasma*, or *Sporothrix*.

When the heterologous nucleic acid sequence encodes a plant protein, the plant protein can be any suitable protein naturally produced by a plant, so long as it is toxic to animal cells (e.g., human cells). Suitable plant toxins include, but are not limited to, lectins (e.g., ricin or abrin), alkaloids, glycosides, oxalates, phenols, resins, volatile oils, and phototoxins (e.g., coumarins).

The heterologous nucleic acid sequence also can encode an animal protein. In this regard, certain animal proteins are inhibitory to adenovirus replication when such proteins are produced in packaging cells. The heterologous nucleic acid sequence can encode any suitable animal protein. Examples of suitable animal proteins include, but are not limited to transforming growth factor β (TGFβ), or nitric oxide synthase (NOS).

In another embodiment, the heterologous nucleic acid sequence can encode an antibiotic. The antibiotic can be isolated from nature, synthetically generated, isolated from a genetically engineered organism, and the like. The heterologous nucleic acid sequence can encode any suitable antibiotic. Suitable antibiotics include, but are not limited to, penicillin, ampicillin, cephalosporin, griseofulvin, bacitracin, polymyxin B, amphotericin B, erythromycin, neomycin, streptomycin, tetracycline, vancomycin, gentamicin, rifamycin, and the like.

One of ordinary skill in the art will appreciate that many of the aforementioned proteins, and portions thereof, can be antigenic when produced in an animal (e.g., mammalian) cell. An "antigen" is a molecule that triggers an immune response in a mammal. An "immune response" can entail, for example, antibody production and/or the activation of immune effector cells. Thus, the heterologous nucleic acid sequence can encode an antigen which comprises any subunit of any proteinaceous molecule, including a protein or peptide of viral, bacterial, parasitic, fungal, protozoan, prion, cellular, or extracellular origin, which ideally provokes an immune response in mammal, preferably leading to protective immunity. The heterologous nucleic acid sequence also can encode a self antigen, i.e., an autologous protein which the body reacts to as if it is a foreign invader.

Preferably, the nucleic acid is operably linked to (i.e., under the transcriptional control of) one or more promoter and/or enhancer elements, for example, as part of a promoter-variable expression cassette. Techniques for operably linking sequences together are well known in the art. A "promoter" is a DNA sequence that directs the binding of RNA polymerase and thereby promotes RNA synthesis. A nucleic acid sequence is "operably linked" to a promoter when the promoter is capable of directing transcription of that nucleic acid sequence. A promoter can be native or non-native to the nucleic acid sequence to which it is operably linked.

Any promoter (i.e., whether isolated from nature or produced by recombinant DNA or synthetic techniques) can be used in connection with the invention to provide for transcription of the nucleic acid sequence. The promoter preferably is capable of directing transcription in a eukaryotic (desirably mammalian) cell. The functioning of the promoter can be altered by the presence of one or more enhancers and/or silencers present on the vector. "Enhancers" are cis-acting elements of DNA that stimulate or inhibit transcription of adjacent genes. An enhancer that inhibits transcription also is termed a "silencer." Enhancers differ from DNA-binding sites for sequence-specific DNA binding proteins found only in the promoter (which also are termed "promoter elements") in that enhancers can function in either orientation, and over distances of up to several kilobase pairs (kb), even from a position downstream of a transcribed region.

Promoter regions can vary in length and sequence and can further encompass one or more DNA binding sites for sequence-specific DNA binding proteins and/or an enhancer or silencer. Enhancers and/or silencers can similarly be present on a nucleic acid sequence outside of the promoter per se. Desirably, a cellular or viral enhancer, such as the cytomegalovirus (CMV) immediate-early enhancer, is positioned in the proximity of the promoter to enhance promoter activity. In addition, splice acceptor and donor sites can be present on a nucleic acid sequence to enhance transcription.

Any suitable promoter or enhancer sequence can be used in the context of the invention. In this respect, the heterologous nucleic acid sequence can be operably linked to a viral promoter. Suitable viral promoters include, for instance, cytomegalovirus (CMV) promoters, such as the CMV immediate-early promoter (described in, for example, U.S. Pat. Nos. 5,168,062 and 5,385,839, and GenBank accession number X17403), promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the Lap2 promoter or the herpes thymidine kinase promoter (Wagner et al., *Proc. Natl. Acad. Sci.*, 78, 144-145 (1981)), promoters derived from SV40 or Epstein Barr virus, an adeno-associated viral promoter, such as the p5 promoter, and the like.

Alternatively, the heterologous nucleic acid sequence can be operably linked to a cellular promoter, i.e., a promoter that drives expression of a cellular protein. Preferred cellular promoters for use in the invention will depend on the desired expression profile to produce the antigen(s). In one aspect, the cellular promoter is preferably a constitutive promoter that works in a variety of cell types, such as immune cells. Suitable constitutive promoters can drive expression of genes encoding transcription factors, housekeeping genes, or structural genes common to eukaryotic cells. For example, the Ying Yang 1 (YY1) transcription factor (also referred to as NMP-1, NF-E1, and UCRBP) is a ubiquitous nuclear transcription factor that is an intrinsic component of the nuclear matrix (Guo et al., *PNAS*, 92, 10526-10530 (1995)). While the promoters described herein are considered as constitutive promoters, it is understood in the art that constitutive promoters can be upregulated. Promoter analysis shows that the elements critical for basal transcription reside from −277 to +475 of the YY1 gene relative to the transcription start site from the promoter, and include a TATA and CCAAT box. JEM-1 (also known as HGMW and BLZF-1) also is a ubiquitous nuclear transcription factor identified in normal and tumorous tissues (Tong et al., *Leukemia*, 12(11), 1733-1740 (1998), and Tong et al., *Genomics*, 69(3), 380-390 (2000)). JEM-1 is involved in cellular growth control and maturation, and can be upregulated by retinoic acids. Sequences responsible for maximal activity of the JEM-1 promoter have been located at −432 to +101 of the JEM-1 gene relative the transcription start site of the promoter. Unlike the YY1 promoter, the JEM-1 promoter does not comprise a TATA box. The ubiquitin promoter, specifically UbC, is a strong constitutively active promoter functional in several species. The UbC promoter is further characterized in Marinovic et al., *J. Biol. Chem.*, 277(19), 16673-16681 (2002).

In the inventive method, the heterologous nucleic acid sequence is operably linked to a promoter and one or more operator sequences of the tetracycline operon (tetO). The tetracycline operon was originally identified in the Tn10 transposon, in which it regulates the expression of tetracycline resistance genes (see, e.g., Hillen et al. in *Protein-Nucleic Acid Interaction, Topics in Molecular and Structural Biology*, Saenger et al., eds., Vol. 10, 143-162, Macmillan, London (1989)). The tetracycline operon, and modified forms thereof, are used in the art to regulate gene expression in recombinant DNA systems. In this regard, the tetracycline regulation system consists of two components: operator sequences (tetO) and a repressor protein (tetR). In the absence of tetracycline, the tetR protein is able to bind to the tetO sites and repress transcription of a gene operably linked to the tetO sites. In the presence of tetracycline, however, a conformational change in the tetR protein prevents it from binding to the operator sequences, allowing transcription of operably linked genes to occur. The tetracycline regulation system has been modified for use in mammalian cells by the generation of a fusion protein combining tetR with the transcriptional activation domain of the VP16 protein of herpes simplex virus, which also is referred to as the tet transactivator protein (tTa) (see, e.g., Gossen and Bujard, *Proc. Natl. Acad. Sci. USA*, 89, 5547-5551 (1992), and Shockett and Schatz, *Proc. Natl. Acad. Sci. USA*, 93, 5173-5176 (1996)).

The heterologous nucleic acid sequence can be operably linked to any suitable tetO site and any suitable number of tetO sites, so long as expression of the heterologous nucleic acid sequence is inhibited in the presence of tetR. In a preferred embodiment of the invention, the heterologous nucleic acid sequence is operably linked to one or more tetO sites, each of which comprises the nucleotide sequence AGCTCTCCCTATCAGTGATAGAGATCTC-CCTATCAGTGATAGAGATCGTCGACGA GCT (SEQ ID NO: 1). The heterologous nucleic acid sequence preferably is operably linked to at least one (e.g., 1, 2, 3, 4, 5, 6, or more) tetO sequence, but more preferably is operably linked to at least two (e.g., 2, 3, 4, 5, 6, or more) tetO sequences.

The one or more tetO sequences can be located in any suitable position with respect to the heterologous nucleic acid sequence and the promoter. In this regard, the tetO sequences can be located upstream of both the promoter and the heterologous nucleic acid sequence. Alternatively, the tetO sequences can be located between the promoter and the heterologous nucleic acid sequence. In another embodiment, the one or more tetO sequences can be located downstream of both the promoter and the heterologous nucleic acid sequence. In addition, the one or more tetO sequences need not be positioned in tandem. For example, one tetO sequence can be located upstream of the promoter, while a second tetO sequence can be located downstream of the promoter and upstream of the heterologous nucleic acid sequence.

Operable linkage of a heterologous nucleic acid sequence to a promoter and tetO sequences is within the skill of the art, and can be accomplished using routine recombinant DNA techniques, such as those described in, for example, Sambrook et al., *Molecular Cloning, a Laboratory Manual*, 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994).

To optimize protein production, preferably the heterologous nucleic acid sequence further comprises a polyadenylation site following the coding sequence of the heterologous nucleic acid sequence. Any suitable polyadenylation sequence can be used, including a synthetic optimized sequence, as well as the polyadenylation sequence of BGH (Bovine Growth Hormone), polyoma virus, TK (Thymidine Kinase), EBV (Epstein Barr Virus), and the papillomaviruses, including human papillomaviruses and BPV (Bovine Papilloma Virus). A preferred polyadenylation sequence is the SV40 (Human Sarcoma Virus-40) polyadenylation sequence. Also, preferably all the proper transcription signals (and translation signals, where appropriate) are correctly arranged such that the nucleic acid sequence is properly expressed in the cells into which it is introduced. If desired, the nucleic acid sequence also can incorporate splice sites (i.e., splice acceptor and splice donor sites) to facilitate mRNA production.

The construction of adenoviral vectors is well understood in the art. Adenoviral vectors can be constructed and/or purified using the methods set forth, for example, in U.S. Pat. Nos. 5,965,358, 6,168,941, 6,329,200, 6,383,795, 6,440,728, 6,447,995, 6,475,757, 6,573,092, and 6,586,226, and U.S. Patent Application Publication Nos. 2003/0170899 A1, 2003/0203469 A1, and 2003/0203480 A1, and International Patent Application Publications WO 98/53087, WO 98/56937, WO 99/15686, WO 99/54441, WO 00/12765, WO 01/77304, WO 02/29388, WO 02/31169, and WO 03/39459 as well as the other references identified herein. Non-group C adenoviral vectors, including adenoviral serotype 35 vectors, can be produced using the methods set forth in, for example, U.S. Pat. Nos. 5,837,511 and 5,849,561, and International Patent Application Publications WO 97/12986 and WO 98/53087. Moreover, numerous adenoviral vectors are available commercially.

The inventive method further comprises providing a cell having a cellular genome comprising a nucleic acid sequence encoding a tetracycline operon repressor protein (tetR). The cell can be any suitable cell which can propagate adenoviral vectors when infected with such vectors or with nucleic acid sequences encoding the adenoviral genome. In this regard, the cell desirably comprises a genome that can incorporate and preferably retain a nucleic acid encoding an adenoviral gene product that complements in trans for a deficiency in one or more regions of an adenoviral genome. Most preferably, the cell can propagate a suitable replication-deficient adenoviral vector upon infection with an appropriate replication-deficient adenoviral vector or transfection with an appropriate replication-deficient viral genome.

Particularly desirable cell types are those that support high levels of adenovirus propagation. The cell preferably produces at least about 10,000 viral particles per cell and/or at least about 3,000 focus forming units (FFU) per cell. More preferably, the cell produces at least about 100,000 viral particles per cell and/or at least about 5,000 FFU per cell. Most preferably, the cell produces at least about 200,000 viral particles per cell and/or at least about 7,000 FFU per cell.

Preferably, the cell is, or is derived from, an anchorage dependent cell, but which has the capacity to grow in suspension cultures. In one embodiment, the cell can be a primary cell. By "primary cell" is meant that the cell does not replicate indefinitely in culture. Examples of suitable primary cells include, but are not limited to, human embryonic kidney (HEK) cells, human retinal cells, and human embryonic retinal (HER) cells. In another embodiment, the cell can be a transformed cell. The cell is "transformed" in that the cell has the ability to replicate indefinitely in culture. Examples of suitable transformed cells include renal carcinoma cells, CHO cells, KB cells, HEK-293 cells, SW-13 cells, MCF7 cells, HeLa cells, Vero cells, neural cells (e.g., BE(2)-M17 cells and SK-N-MC cells), and lung carcinoma cells. Complementing cell lines for producing the adenoviral vector include, but are not limited to, 293 cells (described in, e.g., Graham et al., *J. Gen. Virol.*, 36, 59-72 (1977)), PER.C6 cells (described in, e.g., International Patent Application WO 97/00326, and U.S. Pat. Nos. 5,994,128 and 6,033,908), and 293-ORF6 cells (described in, e.g., International Patent Application WO 95/34671 and Brough et al., *J. Virol.*, 71, 9206-9213 (1997)). Additional complementing cells are described in, for example, U.S. Pat. Nos. 6,677,156 and 6,682,929, and International Patent Application Publication WO 03/20879.

The cell comprises a cellular genome comprising a nucleic acid sequence encoding a tetracycline operon repressor protein (tetR). Like the tetO sequence, the tetR protein was originally identified in the Tn10 transposon as part of the tetracycline operon (see Hillen et al., supra). The tetR protein preferably comprises the amino acid sequence of SEQ ID NO: 2 (GenBank Accession No. J01830, GI No. 154846).

While it is preferred that the nucleic acid sequence encoding the tetR protein encodes a wild-type tetR protein (such as is set forth in SEQ ID NO: 2), the nucleic acid sequence alternatively can encode any suitable variant of the tetR protein. A variant of the tetR protein retains the ability to bind to tetO sequences and repress transcription of a nucleic acid sequence operably linked thereto. A variant tetR protein preferably is produced by introducing one or more mutations (e.g., point mutations, deletions, insertions, etc.) into the nucleic acid sequence encoding a wild type tetR protein. Such mutations are introduced in the nucleic acid sequence to effect one or more amino acid substitutions in an encoded tetR protein. Thus, where mutations are introduced in the nucleic acid sequence encoding the tetR protein, such mutations desirably will effect a substitution in the encoded tetR protein whereby codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. In addition, the nucleic acid sequence can encode a homolog of a tetR protein. A homolog of a tetR protein, whether wild-type or mutant, can be any peptide, polypeptide, or portion thereof, that is more than about 70% identical (preferably more than about 80% identical, more preferably more than about 90% identical, and most preferably more than about 95% identical) to the tetR protein at the amino acid level. The degree of amino acid identity can be determined using any method known in the art, such as the BLAST sequence database. Furthermore, a homolog of the tetR protein can be any peptide, polypeptide, or portion thereof, which hybridizes to the tetR protein under at least moderate, preferably high, stringency conditions. Exemplary moderate stringency conditions include overnight incubation at 37° C. in a solution comprising 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C., or substantially similar conditions, e.g., the moderately stringent conditions described in Sambrook et al., supra. High stringency conditions are conditions that use, for example (1) low ionic strength and high temperature for washing, such as 0.015 M sodium chloride/0.0015 M sodium citrate/0.1% sodium dodecyl sulfate (SDS) at 50° C., (2) employ a denaturing agent during hybridization, such as formamide, for example, 50% (v/v) formamide with 0.1% bovine serum albumin (BSA)/0.1% Ficoll/0.1% polyvinylpyrrolidone (PVP)/50 mM sodium phosphate buffer at pH 6.5 with 750 mM sodium chloride and 75 mM sodium citrate at 42° C., or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at (i) 42° C. in 0.2×SSC, (ii) 55° C. in 50% formamide, and (iii) 55° C. in 0.1×SSC (preferably in combination with EDTA). Additional details and an explanation of stringency of hybridization reactions are provided in, e.g., Ausubel et al., supra.

Replication-deficient adenoviral vectors are typically produced in complementing cell lines that provide gene functions not present in the replication-deficient adenoviral vectors, but required for viral propagation, at appropriate levels in order to generate high titers of viral vector stock. Thus, in addition to the nucleic acid sequence encoding a tetR protein, the cell preferably comprises, integrated into the cellular genome, adenoviral nucleic acid sequences which encode gene functions required for adenoviral propagation. A preferred cell complements for at least one and preferably all replication-essential gene functions not present in a replication-deficient adenovirus. The cell can complement for a deficiency in at least one replication-essential gene function encoded by the early regions, late regions, viral packaging regions, virus-associated RNA regions, or combinations thereof, including all adenoviral functions (e.g., to enable propagation of adenoviral amplicons). Most preferably, the cell complements for a deficiency in at least one replication-essential gene function (e.g., two or more replication-essential gene functions) of the E1 region of the adenoviral genome, particularly a deficiency in a replication-essential gene function of each of the E1A and E1B regions. In addition, the cell can complement for a deficiency in at least one replication-essential gene function of the E2 (particularly as concerns the adenoviral DNA polymerase and terminal protein) and/or E4 regions of the adenoviral genome.

Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome. The ORF-6 of the E4 region of the adenoviral genome preferably is an ORF-6 of the E4 region of a human adenoviral genome, such as a serotype 5 or serotype 2 adenoviral genome. In addition, the ORF-6 of the E4 region of the adenoviral genome can be operably linked to any suitable promoter, but preferably is operably linked to an inducible promoter. Any suitable inducible promoter may be used to regulate the ORF-6 of the E4 region of the adenoviral genome, and suitable inducible promoters are known in the art. In a preferred embodiment of the invention, the inducible promoter is a sheep metallothionine promoter.

The cell preferably is further characterized in that it contains the complementing genes in a non-overlapping fashion with the adenoviral vector, which minimizes, and practically eliminates, the possibility of the vector genome recombining with the cellular DNA. Accordingly, the presence of replication competent adenoviruses (RCA) is minimized if not avoided in the vector stock, which, therefore, is suitable for certain therapeutic purposes, especially vaccination purposes. The lack of RCA in the vector stock avoids the replication of the adenoviral vector in non-complementing cells.

Construction of such a complementing cell involves standard molecular biology and cell culture techniques, such as those described by Sambrook et al., supra, and Ausubel et al., supra).

In some instances, the cellular genome need not comprise nucleic acid sequences, the gene products of which complement for all of the replication-essential deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the desired adenoviral vector. Helper virus is often engineered to prevent packaging of infectious helper virus. For example, one or more replication-essential gene functions of the E1 region of the adenoviral genome can be provided by the complementing cell, while one or more replication-essential gene functions of the E4 region of the adenoviral genome can be provided by a helper virus.

In accordance with the inventive method, the adenoviral vector contacts the cell so as to transfect the cell with the adenoviral vector, such that (a) the nucleic acid sequence encoding tetR is expressed to produce tetR, (b) expression of the heterologous nucleic acid sequence is inhibited in the presence of tetR, and (c) the adenoviral vector is propagated. The cell can be contacted with the adenoviral vector using any suitable method known in the art. Preferably, the cell is transfected with the adenoviral vector in vitro using standard techniques (e.g., calcium phosphate precipitated transfection).

Upon uptake of the adenoviral vector by the cell, the tetR protein produced by the cell desirably binds to the one or more tetO sequences operably linked to the heterologous nucleic acid sequence of the adenoviral vector. As discussed above, tetR binding to tetO sequences prevents the transcriptional machinery from accessing the promoter operably linked to the heterologous nucleic acid sequence, thereby inhibiting expression of the heterologous nucleic acid sequence. The expression of the heterologous nucleic acid sequence is "inhibited" when the level of expression (typically and preferably transcription) of the heterologous nucleic acid sequence in the presence of tetR is at most about 80% (e.g., no more than about 80%, about 70%, or about 60%) the level of expression of the heterologous nucleic acid sequence in the absence of tetR. Preferably, the level of expression of the heterologous nucleic acid sequence in the presence of tetR is at most about 50% (e.g., no more than about 50%, about 40%, or about 30%) the level of expression of the heterologous nucleic acid sequence in the absence of tetR. More preferably, the level of expression of the heterologous nucleic acid sequence in the presence of tetR is at most about 20% (e.g., no more than about 20%, about 10%, about or about 5%) the level of expression of the heterologous nucleic acid sequence in the absence of tetR. Ideally, expression of the heterologous nucleic acid sequence is completely inhibited in the presence of tetR.

One of ordinary skill in the art will appreciate that expression of the nucleic acid sequence encoding the tetR protein in the cell increases the yield of adenoviral vectors encoding the heterologous nucleic acid sequence per cell when compared to the yield of adenoviral vectors per cell when the nucleic acid sequence encoding tetR is not expressed in the cell. Expression of the tetR protein preferably increases the yield of adenoviral vector at least about 5-fold, and more preferably increases the yield of adenoviral vector at least about 20-fold, as compared to the yield of adenoviral vectors when the cell does not express the tetR protein.

The invention further provides a system comprising a cell comprising a cellular genome comprising a nucleic acid sequence encoding a tetracycline operon repressor protein (tetR), which can be expressed to produce tetR, and an adenoviral vector. The adenoviral vector has an adenoviral genome comprising a heterologous nucleic acid sequence encoding a protein that is toxic to the cell, wherein the heterologous nucleic acid sequence is operably linked to a promoter and one or more tetracycline operon operator sequences (tetO), and wherein the adenoviral vector can transfect the cell and be propagated in the cell. Descriptions of the adenoviral vector, the tetO sequences, the cell, and the tetR protein set forth above in connection with other embodiments of the invention also are applicable to those same aspects of the aforesaid system.

The following examples further illustrate the invention but, of course, should not be construed as in any way limiting its scope.

EXAMPLE 1

This example demonstrates a method of inhibiting gene expression from an adenoviral vector according to the inventive method.

An oligonucleotide containing two copies of the tet operator (5'-AGCTCTCCCTATCAGTGATAGAGATCTC-CCTATCAGTGATAGAGATCGTCGACGAGCT-3') (SEQ ID NO: 1) was self-annealed, digested with SacI, and inserted at the SacI site between the TATA box and transcription start site of the CMV enhancer/promoter (GenBank X17403, nucleotides 174,314 to 173,566). An artificial untranslated sequence (UTR) of 144 base pairs and 3' splice site sequences were inserted downstream of the CMV sequences, followed by a nucleic acid sequence encoding green fluorescent protein (GFP) and a simian virus-40 (SV40) polyadenylation signal. The resulting CMV-tetO expression cassette was transferred to a shuttle plasmid containing adenovirus type 5 nucleotides 1-355 and 3333-5793 or 3511-5793 flanking the expression cassette and a restriction site for linearization.

Adenoviral vector genomes were constructed using the AdFast method (see U.S. Pat. No. 6,329,200). Briefly, *E. coli* strain BJDE3 was transfected with 100 ng of shuttle plasmid containing the CMV-tetO expression cassette and 100 ng of a GV.11 base plasmid. The desired recombinant plasmids, containing deletions in the E1, E3, and E4 regions of the adenoviral genome and the expression cassette were identified by restriction digestion of DNA from individual bacterial colonies. The plasmids were further purified by transformation of recombination negative DH5a *E. coli* and single-colony isolation by standard microbiological methods. Isolation of a single genetic clone of the final vector genome was achieved by two sequential colony-growth steps in bacteria. The adenoviral vector plasmid structures were confirmed by restriction digestion analysis and DNA sequencing.

Cell populations of 293 and 293-ORF6 (293 cells that express the Ad5 34 kDa E4 ORF6 protein (Brough et al., *J. Virol.*, 70, 6497-6501 (1996)) carrying the episomal plasmid pREPrsv(Koz-tetR)BghpA (293TetR and 293-ORF6TetR, respectively) were generated by transfection of 2 µg of circular plasmid and addition of hygromycin to 150 µg/ml in the cell culture medium. The transfected cell populations were maintained under hygromycin selection. The expression of tetR protein was confirmed by Western blot analysis of 293TetR and 293-ORF6TetR extracts, which demonstrated that the cell lines that maintained the tetR episome were expressing tetR protein. To generate the stable transfectant cell line, 293-ORF6NT, 293-ORF6 cells were transfected with 2 µg of HpaI-linearized pRSVTetR.hyg plasmid. After 24 hours the cells were split to ten 10 cm dishes and incubated in 250 µg/ml hygromycin.

To demonstrate functional repressor activity, 293TetR cells were transduced with the above-described E1-, E3-, E4-deleted, adenoviral vectors (Rasmussen et al., *Cancer Gene Ther.*, 9, 951-957 (2002)) comprising a nucleic acid sequence encoding GFP expressed under the control of either a CMV promoter (Adf.11D) or the CMV-tetO promoter (AdtetO.f.11D). The fluorescence intensity of 293TetR cells transduced with AdtetO.f.11D was much lower than that of cells transduced by Adf.11D. The addition of 2 µg/ml doxycycline (dox) to cultures of 293TetR cells transduced by the AdtetO.f.11D adenoviral vector resulted in fluorescent intensity similar to that of 293TetR cells transduced by Adf.11D.

To determine whether the lower protein levels observed with the tetR/tetO system were due to reduced levels of transcription, the relative steady-state levels of GFP mRNA were determined by Northern blot analysis of cells productively infected with 1 or 10 focus forming units (FFU) per cell of AdtetO.f.11D. Steady-state GFP mRNA was reduced early (6 hours post-infection or h.p.i.) and late (24 h.p.i.) in 293-ORF6TetR cells compared to 293-ORF6. Thus, the lower level of protein products during virus replication was due to repression of transcription. Moreover, binding of tetR protein to adenovirus DNA did not affect virus propagation or growth since there was no difference between marker gene vectors with and without the tetR/tetO system.

The results of this example demonstrate that gene expression from an adenoviral vector comprising tetO sequences can be inhibited in cells expressing a functional tetR protein.

EXAMPLE 2

This example demonstrates a method of inhibiting gene expression from an adenoviral vector according to the inventive method.

293 cells expressing tetR (293TetR) and lacking tetR (293BB) were generated as described in Example 1. Cells were infected with E1-deleted adenoviral vectors that expressed secreted alkaline phosphatase (SEAP) from constitutive (AdSeap) and regulatable (AdTetO.Seap) expression cassettes. The level of SEAP activity in the culture medium was determined (Phospha-Light™ Kit, Applied Biosystems, Foster City, Calif.) at three early phase time points: 8, 10, and 12 hours post-infection (h.p.i.) and at one time point after significant DNA replication (24 h.p.i.). The level of SEAP activity was specifically reduced in the 293TetR cells infected with AdtetO.Seap. SEAP activity was not reduced in 293BB cells infected with AdtetO.Seap, as compared to 293BB cells infected with AdSeap. The level of SEAP activity was reduced by the tetO vector-tetR cell combination more than 10-fold at the early time points, although the reduction in activity decreased to approximately 3-fold by 24 h.p.i. There was no effect of the repressor on SEAP expression from the adenoviral vector that did not contain tetO sequences (i.e., AdSeap+293TetR compared to AdSeap+293BB).

Similar experiments were performed using E1-, E3-, E4-deleted adenoviral vectors. In particular, 293-ORF6 cells and 293-ORF6TetR cells (see Example 1) were infected with SEAP-encoding adenoviral vectors AdS.11D and AdTetO.S.11D. AdS.11D and AdTetO.S.11D expressed comparable amounts of SEAP in 293-ORF6 cells. In 293-ORF6TetR cells, the expression of SEAP by AdTetO.S.11D was significantly reduced as compared to SEAP expression by AdTetO.S.11D in 293-ORF6 cells. The greatest differences in SEAP activity between AdTetO.S.11D infected 293-

ORF6 and 293-ORF6TetR cells occurred at the early phase time points of 6 and 8 h.p.i. (>10-fold). SEAP activity was reduced about 7 fold at 12 h.p.i., and about 3-fold at 24 h.p.i. The addition of 2 µg/ml doxycycline (dox) to cultures of 293-ORF6TetR cells at the time of infection with AdTetO.S.11D resulted in the expression of SEAP.

The results of this example demonstrate that gene expression from an adenoviral vector comprising tetO sequences can be inhibited in cells expressing a functional tetR protein early in the virus growth cycle. The results of this example also suggest that inhibition of gene expression is affected by the number of vector genomes present within the cell.

EXAMPLE 3

This example demonstrates a method of propagating an adenoviral vector comprising a nucleic acid sequence encoding a toxic protein in accordance with the inventive method.

Seven adenoviral vectors comprising an expression cassette under the control of a CMV promoter inserted into a deleted E1 region could not be propagated to form a stock of viable adenoviral vectors using standard 293 or 293-ORF6 cells. The transgenes encoded by the adenoviral vectors included human transforming growth factor beta-1 (TGFβ) (Wettergreen et al., Eur. J. Oral Sci., 109, 415-421 (2001), two peptide antibiotics, two viral envelope glycoproteins, and two malaria parasite proteins. In contrast, adenoviral vectors encoding each of these genes could be propagated using the tetR/tetO system described herein. To illustrate, an E1-deleted adenoviral vector comprising the CMV-tetO expression cassette was constructed in accordance with the description herein (see, e.g., Example 1). The adenoviral vector encoded an activated form of TGFβ known to have a three to five-fold higher biological activity than wild-type TGFβ (Brunner et al., J. Biol. Chem., 264, 13660-13664 (1989)) (AdtetO.T-GFβ). To determine the effect of high level TGFβ expression on adenoviral vector propagation, 293 and 293TetR cells were infected with AdtetO.TGFp. At 12 hours post-infection, approximately 1.7-fold more TGFβ was detected in the culture medium of 293 cells as compared to 293TetR cells. However, by 24 h.p.i., significantly more TGFβ had accumulated in the culture medium of 293TetR cells (t-test, p=0.01). Despite the high level of TGFβ protein accumulation, there was a 3-fold higher yield of infectious viral particles from 293TetR cells at 24 hours post-infection.

The results of this example demonstrate that an adenoviral vector encoding a toxic protein (such as TGFβ) can be propagated in accordance with the inventive method. The results of this example also suggest that adenoviral propagation is less refractory to toxic protein, specifically TGFβ, inhibition late in infection.

EXAMPLE 4

This example demonstrates a method of propagating an adenoviral vector comprising a nucleic acid sequence encoding a toxic protein in accordance with the inventive method.

An adenoviral vector expressing high levels of a modified HIV-1 envelope gene, gp140 (Yang et al., J. Virol., 78, 4029-4036 (2004)) could not be efficiently propagated. Four attempts to propagate the adenoviral vector failed before the fifth attempt was successful. The yield of virus progeny in the fifth attempt was 10-fold lower than expected.

Three different approaches were attempted to overcome the inhibition to vector generation and growth. First, the gp140 nucleic acid sequence was altered to remove potential inhibitory areas of the gp140 envelope protein. Deletion of protein coding regions of gp140 to generate gp140dV12 (Yang et al., supra) resulted in a high level of gp140 gene expression. The second approach entailed deleting the introns from the CMV expression cassette (hCMVΔ) to decrease the level of gp140 expression. This modification resulted in a 10-fold decrease in gp140 expression. While both of these approaches were successful at restoring efficient generation of the adenoviral vectors and improved adenovirus production yield, the modifications to the gp140 coding sequence and expression thereof were significant. In contrast, the third approach, which entailed inhibiting gp140 expression using the tetR/tetO tet system discussed above, resulted in efficient viral propagation and high virus yield without altering the gene product or reducing the potency of the adenoviral vector. A summary of the results is set forth in the following table.

| Adenoviral Vector | Cell Line | Relative Expression (%) | Viral Propagation Success/ Attempts | Relative Viral Yield[a] (# of preparations) |
|---|---|---|---|---|
| hCMV.Luciferase | 293-ORF6 | 100 | 1/1 | 100% (6) |
| hCMV.gp140 | 293-ORF6 | 100 | 1/5 | 6% (3) |
| hCMV.gp140dV12 | 293-ORF6 | 100 | 1/1 | 88% (3) |
| hCMVA.gp140 | 293-ORF6 | 10 | 3/3 | 84% (5) |
| hCMVtetO.gp140 | 293-ORF6 | 100 | 0/1 | n.a. |
| hCMVtetO.gp140 | 293-ORF6TetR | Repressed | 1/1 | 100% (4) |

[a]Relative to the hCMV.Luciferase adenoviral vector

The results of this example demonstrate that an adenoviral vector encoding a toxic protein (such as gp140) can be propagated in accordance with the inventive method.

EXAMPLE 5

This example demonstrates a method of propagating an adenoviral vector comprising a nucleic acid sequence encoding a toxic protein in accordance with the inventive method.

An E1-deleted adenoviral vector encoding human inducible nitric oxide synthase (iNOS) was grown to high titer only if an iNOS inhibitor was included in the culture medium, demonstrating the inhibitory effect of iNOS overexpression on adenoviral vector replication. Even with the use of inhibitors, however, the iNOS adenoviral vector was propagated at a relatively low titer ($10^9$ particle forming units (PFU)/mL) (Shears et al., J. Am. Coll. Surg., 187, 295-306 (1998)). The preparations of adenoviral vectors containing a CMV-iNOS expression cassette were rapidly overtaken by replication competent adenovirus (RCA) and mutated vectors containing deletions of the iNOS expression cassette, implying a selective pressure against the expression of iNOS.

To prevent RCA formation and alleviate the negative effects of iNOS overexpression, an E1-, E3-, and E4-deleted adenoviral vector containing a CMV-TetO-iNOS expression cassette was constructed in accordance with the description herein. In addition, a PCR assay was developed to assess the integrity of the expression cassette. Two AdFAST vector plasmids with identical CMV-tetO-iNOS expression cassettes were generated. The two adenoviral vectors produced via the AdFAST method differed only in the fiber protein, expressing either a wild-type fiber (AdtetO.hiNOS.11D) or a fiber containing a seven amino acid C-terminal addition (AdtetO.hiNOS.F(pK7).11D (Wickham et al., *J. Virol.*, 71, 8221-8229 (1997)).

293-ORF6 and 293-ORF6TetR cells were transfected with each vector, and lysates were passaged in parallel until cytopathic effect (c.p.e.) on the cells was observed. The iNOS adenoviral vectors propagated on 293-ORF6TetR cells achieved sufficient titer in two passages to generate greater than 50% c.p.e. of $1 \times 10^6$ cells. Subsequent generation of cesium chloride purified stocks yielded titers averaging $2.7 \times 10^{11}$ FFU/mL with an average particle:FFU ratio of 8. Transgene expression and activity of iNOS was confirmed by quantitation of total nitric oxide in transduced cell supernatants (R & D Systems, Minneapolis, Minn.). In comparison, growth of the vectors on 293-ORF6 cells was much slower. Although the adenoviral genome of AdtetO.iNOS.F(pK7).11D was detected by a PCR assay throughout the virus passages on 293-ORF6 cells, the vector did not achieve sufficient titer to induce c.p.e. on the cells even after seven passages.

Infected cell lysates of equal vector passage number were assayed for rearrangements of the expression cassette by PCR analysis. The expected full length amplification product was detected with all adenoviral vectors, and there were no unexpected amplicons detectable in the adenoviral vector preparations performed on 293-ORF6TetR cells. However, production and propagation of the iNOS adenoviral vectors on 293-ORF6 cells yielded unexpected amplicons smaller than the full length product (i.e., approximately 2.1 kb in AdtetO.iNOS.11D and approximately 1.1 kb in AdtetO.iNOS.F(pK7).11D). The 2.1 kb and 1.1 kb PCR products were purified from the agarose gel and sequenced. The 2.1 kb amplicon contained a 2.9 kb deletion of the 3-prime end of the expression cassette consisting of 80% of the iNOS ORF and the entire SV40 polyadenylation site. Similarly, the 1.1 kb amplicon contained a 3.8 kb deletion of the 5-prime end of the expression cassette consisting of the CMV promoter, leaving only 232 bases of the CMV enhancer, and the entire iNOS ORF.

In addition, an E1-, E3-deleted CMV-tetO-iNOS adenoviral vector was constructed by the AdFAST method, propagated on 293TetR cells (Wang et al., *Mol. Ther.*, 7, 597-603 (2003)), and was demonstrated to be free of RCA (approximately $10^{10}$ pu tested), and no E1 region deletions were detected by PCR. Thus, as a result of transcriptional repression, the tetR/tetO system was effective in preventing the overgrowth of cultures by adenovectors with non-functional expression cassettes.

The results of this example demonstrate that an adenoviral vector encoding a toxic protein (such as iNOS) can be propagated in accordance with the inventive method.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of propagatin a non-subgroup C adenoviral vector, which method comprises:
   (a) providing a cell comprising a cellular genome comprising a nucleic acid sequence encoding a tetracycline operon repressor protein (tetR),
   (b) expressing the nucleic acid sequence encoding tetR to produce tetR, and
   (c) contacting the cell with a non-subgroup C adenoviral vector in the absence of tetracycline, wherein the non-subgroup C adenoviral vector has an adenoviral genome comprising a heterologous nucleic acid sequence, wherein the heterologous nucleic acid sequence (i) encodes a protein that inhibits propagation of the adenoviral vector in the cell and (ii) is operably linked to a promoter and one or more tetracycline operon operator sequences (tetO), so as to transfect the cell with the non-subgroup C adenoviral vector, wherein expression of the heterologous nucleic acid sequence is inhibited in the presence of tetR, and a non-subgroup C adenoviral vector is propagated,
   wherein the non-subgroup C adenoviral vector is replication-deficient, and
   wherein the non-subgroup C adenoviral vector requires, at most, complementation of the E4 region of the adenoviral genome for replication.

2. The method of 1 wherein the non-subgroup C adenoviral vector lacks all or part of the E3 region of the adenoviral genome.

3. The method of claim 1, wherein the heterologous nucleic acid sequence encodes an env, gag, or pol protein from clades A, B, or C of a human immunodeficiency virus (HIV), or a fusion protein comprising any of the foregoing.

4. The method of claim 1, wherein the heterologous nucleic acid sequence encodes an E protein, an M protein, or a spike protein of a severe acute respiratory syndrome (SARS) virus.

5. The method of claim 1, wherein the heterologous nucleic acid sequence encodes a transforming growth factor β(TGFβ), an antibiotic, a malaria protein, or a nitric oxide synthase.

6. The method of claim 1, wherein the heterologous nucleic acid sequence encodes protein 1A, 1B, 1C, 1D, 2A, 2B, 2C, 3A, 3B, 3C, or 3D of a foot-and-mouth disease virus (FMD).

7. A system comprising:

(a) a cell comprising a cellular genome comprising a nucleic acid sequence encoding a tetracycline operon repressor protein (tetR), which can be expressed to produce tetR, and (b) a non-subgroup C adenoviral vector having an adenoviral genome comprising a heterologous nucleic acid sequence, wherein (1) the heterologous nucleic acid sequence (i) encodes a protein that inhibits propagation of the non-subgroup C adenoviral vector in the cell and (ii) is operably linked to a promoter and one or more tetracycline operon operator sequences (tetO), (2) the non-subgroup C adenoviral vector can transfect the cell and be propagated in the cell, and
(3) the system lacks tetracycline,
wherein the non-subgroup C adenoviral vector is replication-deficient,
wherein the non-subgroup C adenoviral vector requires, at most, complementation of the E4 region of the adenoviral genome for replication.

8. The system of claim 7, wherein the non-subgroup C adenoviral vector lacks all or part of the E3 region of the adenoviral genome.

9. The system of claim 7, wherein the heterologous nucleic acid sequence encodes an env, gag, or pol protein from clades A, B, or C of a human immunodeficiency virus (HIV), or a fusion protein comprising any of the foregoing.

10. The system of claim 7, wherein the heterologous nucleic acid sequence encodes an E protein, an M protein, or a spike protein of a severe acute respiratory syndrome (SARS) virus.

11. The system of claim 7, wherein the heterologous nucleic acid sequence encodes a transforming growth factor β(TGFβ), an antibiotic, a malaria protein, or a nitric oxide synthase.

12. The system of claim 7, wherein the heterologous nucleic acid sequence encodes protein 1A, 1B, 1C, 1D, 2A, 2B, 2C, 3A, 3B, 3C, or 3D of a foot-and-mouth disease virus (FMD).

13. The method of claim 1, wherein the heterologous nucleic acid sequence encodes a viral protein from family Coronaviridae.

14. The method of claim 1, wherein the heterologous nucleic acid sequence encodes a viral protein from family Picornaviridae.

15. The method of claim 14, wherein the heterologous nucleic acid sequence encodes a poliovirus protein.

16. The method of claim 14, wherein the heterologous nucleic acid sequence encodes an aphthovirus protein.

17. The method of claim 16, wherein the heterologous nucleic acid sequence encodes a foot-and-mouth disease viral protein.

18. The method of claim 7, wherein the heterologous nucleic acid sequence encodes a viral protein from family Coronaviridae.

19. The method of claim 7, wherein the heterologous nucleic acid sequence encodes a viral protein from family Picornaviridae.

20. The method of claim 19, wherein the heterologous nucleic acid sequence encodes a poliovirus protein.

21. The method of claim 19, wherein the heterologous nucleic acid sequence encodes an aphthovirus protein.

22. The method of claim 21, wherein the heterologous nucleic acid sequence encodes a foot-and-mouth disease viral protein.

* * * * *

SEQUENCE LISTING

```
<160> NUMBER OF SEQ ID NOS: 2

<210> SEQ ID NO 1
<211> LENGTH: 58
<212> TYPE: DNA
<213> ORGANISM: Escherichia coli

<400> SEQUENCE: 1
agctctccct atcagtgata gagatctccc tatcagtgat agagatcgtc gacgagct        58

<210> SEQ ID NO 2
<211> LENGTH: 207
<212> TYPE: PRT
```

```
<213> ORGANISM: Escherichia coli

<400> SEQUENCE: 2

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
                35                  40                  45

Arg Ala Leu Leu Asp Ala Leu Ala Ile Glu Met Leu Asp Arg His His
            50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
            130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
            195                 200                 205
```